(12) United States Patent
Fang

(10) Patent No.: US 9,102,891 B2
(45) Date of Patent: Aug. 11, 2015

(54) DIESEL FUEL ADDITIVE

(71) Applicant: Xinggao Fang, Richmond, VA (US)

(72) Inventor: Xinggao Fang, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 94 days.

(21) Appl. No.: 14/149,868

(22) Filed: Jan. 8, 2014

(65) Prior Publication Data
US 2014/0123546 A1    May 8, 2014

Related U.S. Application Data

(62) Division of application No. 12/938,590, filed on Nov. 3, 2010, now Pat. No. 8,668,749.

(51) Int. Cl.
*C10L 1/10* (2006.01)
*C10L 1/224* (2006.01)
(Continued)

(52) U.S. Cl.
CPC .............. *C10L 1/232* (2013.01); *C07D 213/55* (2013.01); *C07D 257/06* (2013.01); *C07D 295/185* (2013.01); *C10L 1/10* (2013.01); *C10L 1/106* (2013.01); *C10L 1/14* (2013.01); *C10L 1/143* (2013.01); *C10L 1/1883* (2013.01); *C10L 1/198* (2013.01); *C10L 1/224* (2013.01); *C10L 1/2383* (2013.01); *C10L 1/2387* (2013.01); *C10L 10/00* (2013.01); *C10L 10/04* (2013.01); *C10L 10/06* (2013.01); *C10L 10/18* (2013.01); *C10L 1/1266* (2013.01); *C10L 1/1817* (2013.01); *C10L 1/1905* (2013.01); *C10L 1/221* (2013.01);
(Continued)

(58) Field of Classification Search
CPC .......... C10L 1/232; C10L 1/2387; C10L 1/10; C10L 1/224; C10L 1/106; C10L 1/14; C10L 1/198; C10L 1/143; C10L 1/1883; C10L 1/2383; C10L 1/2222; C10L 1/1817; C10L 1/238; C10L 1/221; C10L 1/2225; C10L 1/1266; C10L 1/1905; C10L 10/18; C10L 10/00; C10L 10/04; C10L 10/224; C10L 10/06; C07D 257/06; C07D 213/55; C07D 295/185
USPC ............................................ 44/331, 337, 418
See application file for complete search history.

(56) References Cited

U.S. PATENT DOCUMENTS

| | | |
|---|---|---|
| 3,551,466 A | 12/1970 | Gee et al. |
| 5,160,350 A | 11/1992 | Stoldt |

(Continued)

FOREIGN PATENT DOCUMENTS

| | | |
|---|---|---|
| EP | 0372651 A2 | 6/1990 |
| EP | 0400869 A2 | 12/1990 |

(Continued)

*Primary Examiner* — Pamela H Weiss
(74) *Attorney, Agent, or Firm* — Luedeka Neely Group, P.C.

(57) ABSTRACT

A diesel fuel additive composition, a fuel containing the fuel additive, a method for improving diesel engine performance using the additive. The diesel fuel additive includes a reaction product of (a) a hydrocarbyl-substituted acylating agent and (b) a reactant selected from the group consisting of a nitrogen-containing compound, a hydroxyl-containing compound, and water that provides a reaction product selected from the group consisting (1) a mono-amide/mono-acid or metal free mono-acid salt thereof, (2) a diacid or metal free diacid salt thereof, and (3) mono-ester/mono-acid or metal free mono-acid salt thereof. The reaction product includes at least about 10 molar percent acid groups based on total moles of the reaction product.

10 Claims, 1 Drawing Sheet

(51) Int. Cl.
*C10L 1/232* (2006.01)
*C07D 213/55* (2006.01)
*C07D 257/06* (2006.01)
*C07D 295/185* (2006.01)
*C10L 1/14* (2006.01)
*C10L 1/188* (2006.01)
*C10L 1/198* (2006.01)
*C10L 1/2383* (2006.01)
*C10L 10/04* (2006.01)
*C10L 10/06* (2006.01)
*C10L 1/2387* (2006.01)
*C10L 10/00* (2006.01)
*C10L 10/18* (2006.01)
*C10L 1/12* (2006.01)
*C10L 1/19* (2006.01)
*C10L 1/222* (2006.01)
*C10L 1/18* (2006.01)
*C10L 1/22* (2006.01)
*C10L 1/238* (2006.01)

(52) U.S. Cl.
CPC ............ *C10L 1/2222* (2013.01); *C10L 1/2225* (2013.01); *C10L 1/238* (2013.01); *C10L 2200/0446* (2013.01); *C10L 2230/22* (2013.01); *C10L 2270/026* (2013.01)

(56) References Cited

U.S. PATENT DOCUMENTS

| | | |
|---|---|---|
| 5,752,989 A | 5/1998 | Henly et al. |
| 5,955,404 A | 9/1999 | Horodsky et al. |
| 6,083,287 A | 7/2000 | Germanaud et al. |
| 6,548,458 B2 | 4/2003 | Loper |
| 7,071,275 B2 | 7/2006 | Rath et al. |
| 2004/0068922 A1* | 4/2004 | Barbour et al. ............ 44/418 |
| 2006/0218854 A1 | 10/2006 | Barbour et al. |
| 2008/0141581 A1* | 6/2008 | Caprotti et al. ............ 44/351 |
| 2009/0235576 A1 | 9/2009 | Volkel et al. |
| 2011/0219674 A1 | 9/2011 | Barbour et al. |
| 2011/0302828 A1 | 12/2011 | Fang et al. |

FOREIGN PATENT DOCUMENTS

| | | |
|---|---|---|
| EP | 0613938 B1 | 9/1994 |
| JP | 2003342246 A | 12/2003 |

* cited by examiner

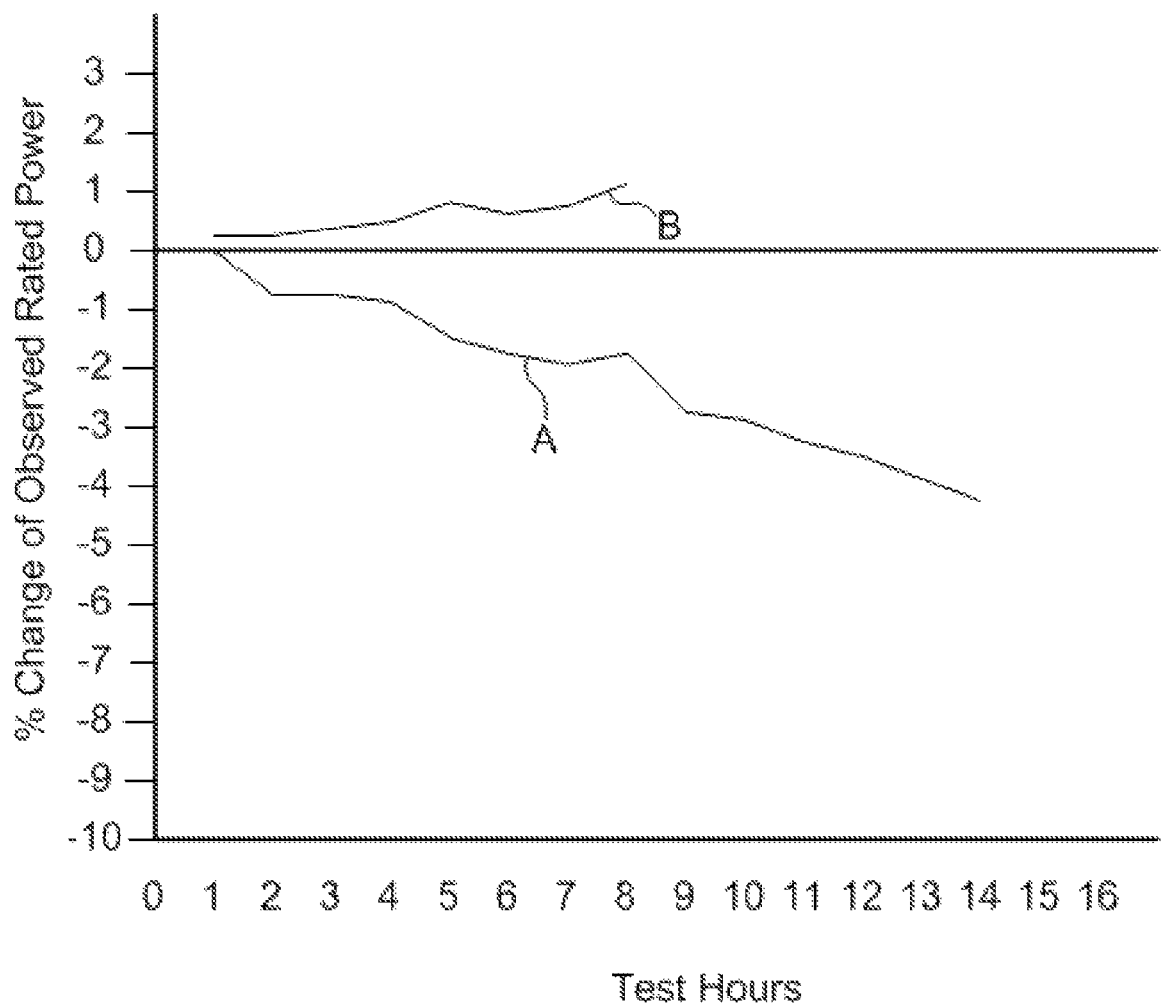

DIESEL FUEL ADDITIVE

RELATED APPLICATION

This application is a division of application Ser. No. 12/938,590, filed Nov. 3, 2010, now U.S. Pat. No. 8,668,749.

TECHNICAL FIELD

The disclosure is directed to certain diesel fuel additives and to diesel fuels and diesel fuel additive concentrates that include the additive. In particular the disclosure is directed to methods for improving the fuel economy and cleanliness of fuel injectors, filters, and fuel delivery systems for compression ignition engines.

BACKGROUND AND SUMMARY

The indirect injection diesel engine has now given way in the market place almost entirely to more modern direct injection light duty diesel engines for reasons of fuel economy, performance, and low emissions. However, direct injection diesel engines are much more sophisticated than the earlier indirect injection engines and require more precise calibration be maintained in order to maintain their design performance. The injectors, key components in the performance of the engine, are vulnerable to having their operation perturbed by fouling from deposits resulting from injection or combustion of fuel.

Direct injection engines may also use a high pressure common rail fuel system or a unity injection system. Recent problems have arisen with the use of low sulfur and ultra low sulfur diesel fuels when used in such high pressure common rail fuel systems. By "high pressure" herein is meant those pressures in diesel fuel systems that are equal to or greater than 15,000 psi (greater than or equal to 1000 bar). Such problems are evident by occurrence of sediment in the fuel additive packages, internal injector deposits, and injector sticking. Accordingly, there was a need to provide fuel additives that are effective to reduce the amount of deposits in the fuel systems and/or effective to clean up fouled fuel systems.

In view of the foregoing and other needs, embodiments of the disclosure provide a diesel fuel additive composition, a fuel containing the fuel additive, a method for improving diesel engine performance using the additive. The diesel fuel additive includes a reaction product of (a) a hydrocarbyl-substituted acylating agent and (b) a reactant selected from the group consisting of a nitrogen-containing compound, a hydroxyl-containing compound, and water that provides a reaction product selected from the group consisting (1) a mono-amide/mono-acid or metal free mono-acid salt thereof, (2) a diacid or metal free diacid salt thereof, and (3) mono-ester/mono-acid or metal free mono-acid salt thereof, wherein the reaction product includes at least about 10 molar percent of acid groups based on total moles of the reaction product.

In another embodiment of the present disclosure provides a method for improving the performance of an engine combusting a diesel fuel having less than 50 ppm by weight or less sulfur, typically less than about 20 ppm sulfur by weight based on a total weight of the fuel. The method includes combining a low sulfur middle distillate fuel with a fuel additive comprising a reaction product of (a) a hydrocarbyl-substituted acylating agent and (b) a reactant selected from the group consisting of a nitrogen-containing compound, a hydroxyl-containing compound, and water that provides a reaction product selected from the group consisting (1) a mono-amide/mono-acid or metal free mono-acid salt thereof, (2) a diacid or metal free diacid salt thereof, and (3) mono-ester/mono-acid or metal free mono-acid salt thereof, wherein the reaction product includes at least about 10 molar percent acid groups based on total moles of the reaction product. The additized fuel is combusted in the engine, whereby the performance of the engine is improved relative to the performance of the engine in the absence of the fuel additive.

Yet another embodiment of the disclosure provides a low sulfur diesel fuel composition suitable for a high pressure compression ignition engine. The diesel fuel composition includes a) a major amount of low sulfur diesel fuel, and b) a minor amount of additive for reducing injector and fuel system deposits. The additive is a reaction product of (i) a hydrocarbyl-substituted acylating agent and (ii) a reactant selected from the group consisting of a nitrogen-containing compound, a hydroxyl-containing compound, and water that provides a reaction product selected from the group consisting (1) a mono-amide/mono-acid or metal free mono-acid salt thereof, (2) a diacid or metal free diacid salt thereof, and (3) mono-ester/mono-acid or metal free mono-acid salt thereof, wherein the reaction product includes at least about 10 molar percent acid groups based on total moles of the reaction product.

Other embodiments of the disclosure provide a method for increasing fuel economy of a vehicle, comprising combusting the diesel fuel composition as described herein wherein said fuel economy increase is defined by power recovery, and said power recovery is greater than 50% as determined by the formula $$\text{Power recovery} = (DU - CU)/DU$$

wherein DU is a percent power loss during a dirty-up phase without the additive, CU is the percent power loss during a clean-up phase with the fuel additive, and power is measured according to CEC F98-08 DW10 test.

According to one or more embodiments of the disclosure, the additive for use in diesel fuel may provide benefits that include, but are not limited to: a) maintaining clean fuel delivery systems including injectors and fuel filters; b) an ability to clean-up dirty or fouled fuel delivery systems; c) a contribution to boosting or increasing fuel economy; d) reducing combustion system deposits; e) reducing fuel system corrosion; f) and improving lubrication of the fuel system and combustion chamber. The additives of the disclosure may provide similar benefits to other middle distillate fuels, such as home heating oils, marine fuel, and jet fuel.

BRIEF DESCRIPTION OF THE DRAWING

FIG. 1 is a graphical illustration of power loss over time for an additive according to the disclosure and a comparative additive in a diesel engine.

DETAILED DESCRIPTION OF DISCLOSED EMBODIMENTS

Further features, embodiments and advantages thereof may be provided by the following detailed description of embodiments of the disclosure. An important feature of the embodiments described herein is that the reaction product used as an additive component of the fuel contains less than about 90 molar percent of an imide and essentially no diamide, or diester components based on a total moles of the reaction product as determined by Fourier transform infrared spectroscopy (FTIR). For example, the reaction product may contain less than 70 molar percent of the imide and suitably from about 0 to about 60 molar percent of imide based on total moles of the reaction product.

Another important feature of the embodiments described herein is that the reaction product contains at least about 10 molar percent acid groups based on total moles of the reaction product. For example, the reaction product may contain from about 10 to about 20 molar percent or more acid groups. In another example the reaction product may contain from about 20 to about 50 molar percent acid groups. In yet another example, the reaction product may contain about 100 molar percent acid groups.

While it is difficult to determine fully the components of the reaction product, for the purposes of this disclosure, the reaction product will be characterized by its primary or major component made from the reactants. For example, depending on the reactant (b), each dicarboxylic acylating agent moiety in the reaction product may be primarily a diacid or a metal-free diacid salt thereof, a mono-amide/mono-acid or metal-free salt thereof, or a mono-ester/mono-acid or metal-free salt thereof as described in more detail below. In each case where the reaction product includes an acid or salt moiety, the acid or salt moiety may actually be a mixture of acid and salt moieties. It will be appreciated that the reaction product may also include unreacted components and/or byproducts that may be a major or minor portion of the reaction product. However, with all of the reactants (b), the reaction product will desirably contain at least one metal-free carboxylic acid group or nitrogen-containing salt thereof.

The first component used to make the reaction product is a hydrocarbyl-substituted acylating agent. The molecular weight of the hydrocarbyl acylating agent may be determined by gel permeation chromatography (GPC). The GPC separation method involves column chromatography in which the stationary phase is a heteroporous, solvent-swollen polymer network of a polystyrene gel varying in permeability over many orders of magnitude. As the liquid phase (tetrahydrofuran) containing the polymer sample passes through the gel, the polymer molecules diffuse into all parts of the gel not mechanically barred to them. The smaller molecules "permeate" more completely and spend more time in the column; the larger molecules "permeate" less and pass through the column more rapidly. The $M_n$ and $M_w$ values of the hydrocarbyl acylating agent may be obtained by comparing distribution data obtained from the GPC to a series of calibration standards of polymers of known molecular weight. The average molecular weight of the hydrocarbyl acylating agent according to the embodiments of the disclosure may be determined by GPC using a polystyrene standard.

For the purposes of the disclosure, the term "hydrocarbyl group" or "hydrocarbyl" is used in its ordinary sense, which is well-known to those skilled in the art. Specifically, hydrocarbyl refers to a group having a carbon atom directly attached to the remainder of a molecule and having a predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every three carbon atoms in the hydrocarbyl group; in some embodiments, there will be no non-hydrocarbon substituent in the hydrocarbyl group.

In an aspect of the disclosed embodiments, the hydrocarbyl substituent of the hydrocarbyl-substituted acylating agent may be derived from an alpha-olefin, internal-olefin, or polyolefin having more than 12 carbon atoms. Non-limiting examples if alpha-olefins include 1-hexadecene, 1-tetradecene, 1-octadecene, and mixtures of $C_{14}$ to $C_{26}$ alpha-olefins. Polyolefins include, but are not limited to, highly branched polyethylene, ethylene alpha-olefin copolymers, polypropylene, and butene polymers, for example polymers of isobutylene. Suitable polyisobutenes for use herein include those formed from polyisobutylene or highly reactive polyisobutylene having at least about 60%, such as about 70% to about 90% and above, terminal vinylidene content. Suitable polyisobutenes may include those prepared using $BF_3$ catalysts. The average number molecular weight of the hydrocarbyl substituent may vary over a wide range, for example from about 100 to about 5000, such as from about 500 to about 5000, as determined by GPC as described above. A particularly useful additive contains polyisobutenyl group of the hydrocarbyl-substituted acylating agent having a number average molecular weight ($M_n$) in the range of from about 350 to 2300 as determined by GPC.

The carboxylate component of the acylating agent may be selected from a dicarboxylic acid or a glycolic acid or anhydride thereof or glyoxal. For example, the carboxylate component may be a succinic acid or anhydride made from maleic acid or anhydride. When the acylating agent is not a succinic acid or anhydride derivative, carboxylic reactants other than maleic anhydride may be employed such as fumaric acid, glutaric acid, glutaconic acid, malic acid, itaconic acid, itaconic anhydride, citraconic acid, citraconic anhydride, mesaconic acid, ethylmaleic anhydride, dimethylmaleic anhydride, ethylmaleic acid, dimethylmaleic acid, hexylmaleic acid, and the like, including the corresponding acid halides and lower aliphatic esters. A mole ratio of maleic anhydride to hydrocarbyl component in the reaction mixture may vary widely. Accordingly, the mole ratio may vary from about 5:1 to about 1:5, for example from about 3:1 to about 1:3, and as a further example, the dicarboxylic component may be used in stoichiometric excess to force the reaction to completion. A particularly useful hydrocarbyl acylating agent may have a molecular weight distribution of weight average molecular weight ($M_w$) to number average molecular weight ($M_n$) of greater than 1.4 ($M_w/M_n$) in the reaction product. The unreacted dicarboxylic component may be removed by vacuum distillation.

As used herein, the term "major amount" is understood to mean an amount greater than or equal to 50 wt. %, for example from about 80 to about 98 wt. % relative to the total weight of the composition. Moreover, as used herein, the term "minor amount" is understood to mean an amount less than 50 wt. % relative to the total weight of the composition.

"Middle distillate fuel" as used herein may be, for example, a naphtha, kerosene or diesel fuel composition. It may be a heating oil, an industrial gas oil, a drilling oil, an automotive diesel fuel, a distillate marine fuel or a kerosene fuel such as an aviation fuel or heating kerosene. It may in particular be a diesel fuel composition. More particularly, a middle distillate fuel is a fuel that is suitable and/or adapted and/or intended for use in an internal combustion engine; for example an automotive fuel composition, and/or adapted and/or intended for use in an automotive diesel (compression ignition) engine. Such middle distillate fuel may be organically or synthetically derived, for example a petroleum derived or Fischer-Tropsch derived gas oil. A middle distillate fuel may have boiling points within the usual diesel range of from 125 or 150 to 400 or 550° C., depending on grade and use. A density of the middle distillate fuel may range from 0.75 to 1.0 g/cm$^3$, for example, from 0.8 to 0.86 g/cm$^3$, at 15° C. and a measured cetane number (ASTM D613) of from 35 to 80, suitably from 40 to 75 or 70. An initial boiling point of a middle distillate fuel may suitably be in the range 150 to 230° C. and the fuel may have a final boiling point in the range 290 to 400° C. A kinematic viscosity of the middle distillate fuel at 40° C. (ASTM D445) might suitably range from 1.5 to 4.5 mm$^2$/s (centistokes).

The diesel fuels of the disclosed embodiments may be applicable to the operation of both stationary diesel engines (e.g., engines used in electrical power generation installations, in pumping stations, etc.) and ambulatory diesel engines (e.g., engines used as prime movers in automobiles, trucks, road-grading equipment, military vehicles, etc.).

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items As set forth above, it has been found, unexpectedly, that reducing the amount of imide reaction product in the additive may provide significant advantages with respect to certain low sulfur diesel fuels, particularly when used in diesel engines having a high pressure common rail injector system. In order to reduce the amount of imide formed in the reaction product, the amount of reactant reacted with the hydrocarbyl acylating agent may be controlled to no more than 1 equivalent per equivalent of hydrocarbyl acylating agent.

In one embodiment, the reaction product used as the additive contains less than about 90 molar percent imide, for example, less than about 70 molar percent imide, and suitably from about 0 to about 60 molar percent imide. The reaction product may also be essentially devoid of diamide reaction products and diester reaction products. In order to provide the foregoing reaction product, the hydrocarbyl acylating agent is reacted with a nitrogen-containing compound, a hydroxyl-containing compound, or water.

The nitrogen-containing compound may be selected from an amine, a polyamine, ammonia, aminoguanidine, piperazine and piperazine derivatives, aminotriazole, morphine, aminotetrazole, hydrazine, guanidine, amino-pyrimidine, and the like. Any of numerous amines, polyamines and the like may be used in preparing the reaction product. Non-limiting examples of amines include methylamine, 2-ethylhexylamine, n-dodecylamine, stearylamine, N,N-dimethyl-propanediamine, N-(3-aminopropyl)morpholine, N-dodecyl-propanediamine, N-aminopropyl-piperazine, and the like.

Non-limiting exemplary polyamines may include aminoguanidine bicarbonate (AGBC), ethylenediamine, diethylene triamine (DETA), triethylene tetramine (TETA), tetraethylene pentamine (TEPA), pentaethylene hexamine (PEHA) and heavy polyamines. A heavy polyamine may comprise a mixture of polyalkylenepolyamines having small amounts of lower polyamine oligomers such as TEPA and PEHA, but primarily oligomers having seven or more nitrogen atoms, two or more primary amines per molecule, and more extensive branching than conventional polyamine mixtures. Additional non-limiting polyamines which may be used to prepare the hydrocarbyl-substituted additive component are disclosed in U.S. Pat. No. 6,548,458, the disclosure of which is incorporated herein by reference in its entirety. In an embodiment of the disclosure, the polyamine may be selected from tetraethylene pentamine (TEPA)

Hydroxyl-containing compounds, include, but are not limited to, ethanolamine, diethanolamine, triethanolamine, N-ethanol-ethylenediamine, $C_1$ to $C_{18}$ alcohols and the like.

In an embodiment, the additive component may include compounds of following formula:

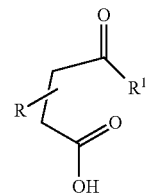

(I)

and ammonia or amine salts thereof, wherein R represents a hydrocarbyl group having 10 or more atoms and R$^1$ represents OH, an alkoxy group, an amine, a polyamine, or an alkoxyamine moiety, provided that R has more than 12 carbon atoms when R$^1$ is OH. For example, when polyisobutylene substituted maleic anhydride is reacted with methyl piperazine, the reaction product may contain a major portion of a compound of the formula:

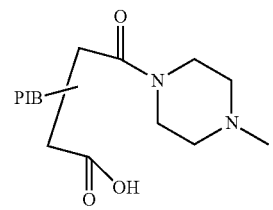

(2)

wherein PIB is a polyisobutylene group. Reaction of polyisobutylene substituted maleic anhydride with aminotetrazole may provide a compound of the formula:

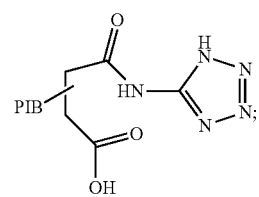

(3)

reaction with 2-hydroxyl ethyl pyridine may provide a compound of the formula:

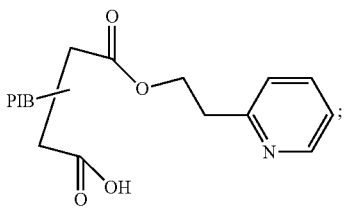

(4)

reaction with triethanolamine may provide a compound of the formula:

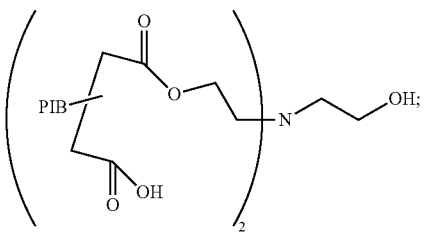

(5)

and reaction with water may provide a compound of the formula:

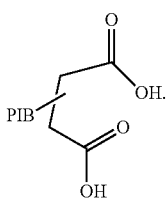

(6)

The foregoing additive may made with a molar ratio of (a) hydrocarbyl-substituted acylating agent to (b) reactant in the reaction medium in the range 10:1 to 1:10. Other reaction conditions are exemplified in the examples contained herein.

When formulating fuel containing the additive as described herein, the fuel may contain an amount of additive ranging from about 10 to about 10,000 ppmw per volume of fuel, such as from about 80 ppmw to about 200 ppmw per volume of fuel. For example, in order to maintain the cleanliness of the fuel system and injectors, the fuel may contain from about 10 to about 100 ppmw per volume of fuel. However, from about 100 to about 200 ppmw per volume of fuel may be used to clean-up a fouled fuel system in order to restore power over a relatively short period of time. In aspects where a carrier is employed to provide a composition containing the additive to the fuel, the additive compositions may contain, on an active ingredients basis, an amount of the carrier ranging from about 10 mg to about 1000 mg of carrier per kg of fuel, such as about 25 mg to about 700 mg of carrier per kg of fuel. The active ingredient basis excludes the weight of (i) unreacted components associated with and remaining in the additives as produced and used, and (ii) solvent(s), if any, used in the manufacture of the disclosed additives either during or after its formation but before addition of a carrier, if a carrier is employed.

The additive of the present disclosure may be blended into a base fuel individually or in various sub-combinations. In some embodiments, the additive of the present disclosure may be blended into a fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

One or more additional optional additives may be present in the fuel compositions disclosed herein. For example, the fuel compositions may contain antifoam agents, additional dispersants, detergents, antioxidants, thermal stabilizers, carrier fluids, metal deactivators, dyes, markers, corrosion inhibitors, biocides, antistatic additives, drag reducing agents, friction modifiers, demulsifiers, emulsifiers, dehazers, anti-icing additives, antiknock additives, surfactants, cetane improvers, corrosion inhibitors, cold flow improvers, pour point depressants, solvents, demulsifiers, lubricity additives, extreme pressure agents, viscosity index improvers, seal swell agents, amine stabilizers, combustion improvers, dispersants, conductivity improvers, organic nitrate ignition accelerators, manganese tricarbonyls compounds, and mixtures thereof. In some aspects, the fuel additive compositions described herein may contain about 10 wt. % or less, or in other aspects, about 5 wt. % or less, based on the total weight of the additive or fuel composition, of one or more of the above additives. Similarly, the fuel compositions may contain suitable amounts of fuel blending components such as methanol, ethanol, dialkyl ethers, and the like.

In order to further illustrate features and advantages of the disclosed embodiments, the following non-limiting examples are provided. For the purposes of the following examples, the molecular weight of the additives was measured by gel permeation chromatography (GPC) with tetrahydrofuran (THF) as a solvent. Polystyrene standards of desired molecular weight ranges were used as the standards.

Comparative Example 1

A fuel additive was produced from the reaction of polyisobutylene succnic anhydride (PIBSA) with a polyamine (PAM), in this case, tetraethylenepentamine (TEPA) in a molar ratio of PIBSA/PAM=1/1. A modified procedure as disclosed in U.S. Pat. No. 5,752,989 was used to make the reaction product as follows: PIBSA (551 g) was diluted in 200 gram of Aromatic 150 solvent under a nitrogen atmosphere. The mixture was heated to 115° C. 112 grams of TEPA was then added through an addition funnel. The addition funnel was rinsed with additional 50 grams of Aromatic 150 solvent. The reaction mixture was heated to 180° C. for about 2 hours under a slow nitrogen sweep. Water was collected in a Dean-Stark trap during the reaction. The product was obtained as a brownish oil. Fourier transform infrared spectroscopy (FTIR) analysis showed an area ratio of imide (1701 cm-1) to amide (1670 cm-1) of 22:1 in the reaction product.

Comparative Example 2

An additive was made as described in Example 1 except that the TEPA was replaced with diethanol amine. FTIR analysis showed a mixture of ester (1735 cm-1) and amide (1637 cm-1) groups and there was no indication of imide, carboxylic acid, or carboxylate functionality in the reaction product.

Comparative Example 3

An additive was made as described in Example 1 except that each mole of TEPA was replaced with 2 moles of 4-methylpiperazine.

Comparative Example 4

An additive was made as described in Example 1. The reaction product was then further reacted with 1,8-naphthalic anhydride per mole of PIBSA in the reaction product.

Comparative Example 5

An additive was made similar to that of Example 1 except that TEPA was replaced with aminoguanidine bicarbonate. The reaction product was then further reacted with 1 mole TEPA per mole of PIBSA in the reaction product.

Comparative Example 6

An additive was made as described in Example 1 except that PIBSA was replaced with an alkenyl succinic anhydride where the alkylenyl group had an average of 16 carbons and TEPA was replaced with a polyetherdiamine.

Comparative Example 7

A mixture was made with the reaction product of Example 1 and a bisaminotriazole that was made following the general procedure of Example 1 in U.S. Pat. No. 5,174,915, with the exception that a 950 molecular weight polyisobutylene (PIB) was used.

Example 8

An additive was made similar to that of Example 1 except that the temperature was not raised to 180° C. during the reaction and no extra effort was made to remove water during the reaction. The reaction product was neutralized with a tertiary amine in a molar ratio of 1/1 (PIBSA/tertiary amine). FTIR analysis showed the area ratio of the imide to amide was about 1:1.

Example 9

An additive was made similar to that of Example 1 except that TEPA was replaced with aminoguanidine bicarbonate.

Example 10

An additive was made as described in Example 1 except that each mole of TEPA was replaced with 1.5 moles of water and reaction was carried out below 80° C. The reaction mixture was filtered through a filter aid.

Example 11

An additive was made as described in Example 10 except that that PIBSA was replaced with an alkenyl succinic anhydride (ASA) having from about 20-24 carbons in the alkenyl group.

Example 12

An additive was made similar to that of Example 1 except that TEPA was replaced with 5-amino-tetrazole.

Example 13

An additive was made as described in Example 11 except that water was replaced with triethanol amine. The mole ratio of ASA to triethanol amine in the reaction mixture was 2 to 1.

Example 14

An additive was made according to Example 3 except that the molar ratio of PIBSA to 4-methyl piperazine used in the reaction mixture was a 1 to 1 molar ratio. FTIR analysis showed acid (1716 cm-1) and amide (1646 cm-1) groups in the reaction product.

Example 15

An additive was made according to Example 14 with the exception that 4-methyl piperazine was replaced by 2-hydroxyethyl pyridine.

Example 16

An additive was made according to Example 1, except that the reaction product was exposed to moisture vapor for an extended period of time. FTIR showed ratio an area ratio of imide (1698 cm-1) to amide (1648 cm-1) of 1:10 in the reaction product.

In the following examples, the effect the additives made according to methods of Examples 8-16 had on diesel fuel for high pressure common rail diesel fuel systems was evaluated. A DW10 test that was developed Coordinating European Council (CEC) was used to demonstrate the propensity of fuels to provoke fuel injector fouling and was also used to demonstrate the ability of certain fuel additives to prevent or control these deposits. An engine dynamometer test stand was used for the installation of the Peugeot DW10 diesel engine for running the CEC F-98-08 tests. The engine was a 2.0 liter engine having four cylinders. Each combustion chamber had four valves and the fuel injectors were DI piezo injectors have a Euro V classification.

The core protocol procedure consisted of running the engine on a fuel containing 1 ppm zinc neodecanoate through a cycle for 8-hours and allowing the engine to soak (engine off) for a prescribed amount of time. The foregoing sequence was repeated four times. At the end of each hour, a power measurement was taken of the engine while the engine was operating at rated conditions. The injector fouling propensity of the fuel was characterized by a difference in observed rated power between the beginning and the end of the test cycle.

Test preparation involved flushing the previous test's fuel from the engine prior to removing the injectors. The test injectors were inspected, cleaned, and reinstalled in the engine. If new injectors were selected, the new injectors were put through a 16-hour break-in cycle. Next, the engine was started using the desired test cycle program. Once the engine was warmed up, power was measured at 4000 RPM and full load to check for full power restoration after cleaning the injectors. If the power measurements were within specification, the test cycle was initiated. The following Table 1 provides a representation of the DW10 coking cycle that was used to evaluate the fuel additives according to the disclosure.

TABLE 1

One hour representation of DW10 coking cycle.

| Step | Duration (minutes) | Engine speed (rpm) | Load (%) | Torque (Nm) | Boost air after IC (° C.) |
|---|---|---|---|---|---|
| 1 | 2 | 1750 | 20 | 62 | 45 |
| 2 | 7 | 3000 | 60 | 173 | 50 |
| 3 | 2 | 1750 | 20 | 62 | 45 |
| 4 | 7 | 3500 | 80 | 212 | 50 |
| 5 | 2 | 1750 | 20 | 62 | 45 |
| 6 | 10 | 4000 | 100 | * | 50 |
| 7 | 2 | 1250 | 10 | 25 | 43 |
| 8 | 7 | 3000 | 100 | * | 50 |
| 9 | 2 | 1250 | 10 | 25 | 43 |
| 10 | 10 | 2000 | 100 | * | 50 |
| 11 | 2 | 1250 | 10 | 25 | 43 |
| 12 | 7 | 4000 | 100 | * | 50 |

Example 17

Diesel engine nozzle coking tests were conducted generally in accordant with the Peugeot DW10 engine following CEC F-98-08 protocol of Table 1 with the exception that the engines were run for only an 8 hour cycle unless noted otherwise. The engine was run with diesel fuel (PC10) with zinc neodecanoate without an additive to establish a baseline. In each of the comparative examples, Runs 1-7, the additive was used at a treat rate of 50 ppmw per volume of fuel. In each of the inventive examples, Runs 8-15, the additive was used at a treat rate of 50 ppmw per volume of fuel. The power loss is an indication of the fouling of the injectors. Ideally, in a keep-clean test, the power decrease should be zero. Negative numbers indicate power loss and positive numbers indicate power increase. Table 2 provides the power changes for comparative examples and Table 3 provides the power changes for examples according to the embodiments of the disclosure.

TABLE 2

| Run No. | Comparative example reaction products | Power change |
|---|---|---|
| 1 | Base fuel | −4.23 |
| 2 | Comparative Example 2 | −3.62 |
| 3 | Comparative Example 3 | −2.81 |
| 4 | Comparative Example 1 (except this was run in the engine for 16 hours) | −4.41 |
| 5 | Comparative Example 4 | −4.67 |
| 6 | Comparative Example 5 | −3.74 |
| 7 | Comparative Example 6 | −3.53 |

TABLE 3

| Run No. | Inventive example reaction products | Power change |
|---|---|---|
| 8 | Example 10 | 0.13 |
| 9 | Example 10 | 1.08 |
| 10 | Example 11 | −1.22 |
| 11 | Example 9 | 1.21 |
| 12 | Example 12 | 0.58 |
| 13 | Example 13 | 0.55 |
| 14 | Example 14 | −085 |
| 15 | Example 15 | −0.14 |

As shown by the significantly low power loss and power increase in Runs 8-15, additives made according to the disclosed embodiments are significantly better at keeping the fuels systems clean than the comparative additives of Runs 1-7. FIG. 1 illustrates the % change in rated power over a sixteen hour test period for Run 4 (A) and Run 9 (B) compared to the ideal power loss of zero.

Example 18

In the following examples, the ability of additives to clean up a dirty fuel system was evaluated according to the test protocol of Example 17. Unless indicated, the comparative examples were obtained by running the engine without additive for 16 hours and then running the engine with the additive for 16 hours and determining the percent power improvement as a result of engine clean-up with the additive. In the inventive examples, the engine was run without additive for 8 hours and then for 8 hours for clean up, unless indicated otherwise. The percent power recovery was determined by the following formula Power recovery=(DU−CU)/DU wherein DU is a percent power loss during a dirty-up phase without the additive, CU is the percent power loss during a clean-up phase with the fuel additive, and power is measured according to CEC F98-08 DW10 test. The comparative examples are shown in Table 4 and the inventive examples are shown in Table 5.

TABLE 4

| Run No. | Comparative example reaction products | Dirty Up | Clean Up | % Power increase |
|---|---|---|---|---|
| 16 | Comparative Example 1 | −4.74 | −4.46 | 5 |
| 17 | Comparative Example 7 | −3.83 | −.302 | 21 |
| 18 | Comparative Example 1 with 32 hour Dirty up and 32 hour Clean up | −6.1 | −4.65 | 24 |

TABLE 5

| Run No. | Inventive example reaction products | Dirty Up | Clean Up | % Power increase |
|---|---|---|---|---|
| 19 | Example 9 | −2.47 | −0.56 | 77 |
| 20 | Example 12 | −2.04 | −0.45 | 78 |
| 21 | Example 8 with a 16 hour Dirty up and 16 hour Clean up | −5.52 | −1.88 | 66 |
| 22 | Example 16 with 32 hour Dirty up and 32 hour Clean up | −5.61 | −2.83 | 50 |

As shown by the foregoing examples Runs 19-22, the inventive additive reaction products provided a significant increase in power compared to the comparative examples of Runs 16-18.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

That which is claimed is:

1. A low sulfur diesel fuel composition suitable for a high pressure compression ignition engine, comprising:
   a) a major amount of low sulfur diesel fuel, and
   b) a minor amount of additive for reducing injector and fuel system deposits, the additive comprising:
      a reaction product of (i) a hydrocarbyl-substituted acylating agent and (ii) a reactant selected from the group consisting of ethylenediamine, diethylene triamine, triethylene tetramine, tetraethylene pentamine, pentaethylene hexamine, ammonia, aminoguanidine bicarbonate, guanidine, piperazine, methylpiperazine, amino-pyrimidine, aminotriazole, and aminotetrazole, $C_2$-$C_3$-alkanolamines, N-ethanol-ethylenediamine, hydroxyethyl pyridine, and water, and mixtures thereof that provides at least 10 molar percent of reaction product based on total moles of the reaction product, said reaction product selected from the group consisting (1) a mono-amide/mono-acid or a mono-amide/metal free mono-acid salt thereof, and (3) monoester/mono-acid or a monoester/metal free mono-acid salt thereof,
      wherein the reaction product is made under conditions sufficient to provide the reaction product with at least 10 molar percent acid groups or nitrogen-containing salt thereof based on total moles of the reaction product.

2. The diesel fuel composition of claim 1, wherein reactant (ii) is selected from the group consisting of ethylenediamine, diethylene triamine, triethylene tetramine, tetraethylene pentamine, pentaethylene hexamine, ammonia, aminoguanidine bicarbonate, piperazine, amino-pyrimidine, aminotriazole, and aminotetrazole.

3. The diesel fuel composition of claim 1, wherein the reaction product is derived from not more than about one equivalent of reactant (ii) per hydrocarbyl-substituted acylating agent.

4. The diesel fuel composition of claim 1, wherein the reaction product contains 0 to less than about 60 percent by weight of an imide based on a total weight of the reaction product.

5. The diesel fuel composition of claim 1, wherein the reaction product comprises at least one compound of the formula (1):

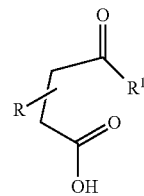

(1)

and ammonia or amine salts thereof, wherein R represents a hydrocarbyl group having 10 or more carbon atoms and $R^1$ represents an alkoxy group, an amine, a polyamine, or an alkoxyamine moiety.

6. The diesel fuel composition of claim 5, wherein the compound of formula (1) is selected from the group consisting of:

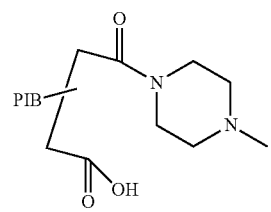

(2)

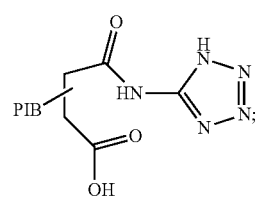

(3)

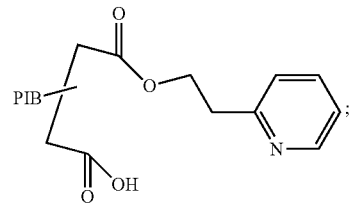

(4)

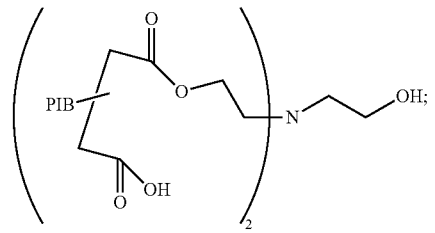

(5)

wherein PIB is a polyisobutylene group.

7. A method for increasing fuel economy of a vehicle, comprising combusting the diesel fuel composition of claim 1 wherein said fuel economy increase is defined by power recovery, and said power recovery is greater than 50% as determined by the formula Power recovery=(DU−CU)/DU wherein DU is a percent power loss during a dirty-up phase without the additive, CU is the percent power loss during a clean-up phase with the fuel additive, and power is measured according to a Coordinating European Council (CEC) F98-08 DW10 test.

8. The composition of claim 1, wherein the hydrocarbyl-substituted acylating agent is selected from the group consisting of hydrocarbyl-substituted malonic anhydride, hydrocarbyl-substituted succinic anhydride, and hydrocarbyl substituted glutaric anhydride.

9. The composition of claim 1, wherein the hydrocarbyl-substituted acylating agent comprises polyisobutenyl-substituted succinic anhydride.

10. The composition of claim 1, wherein the hydrocarbyl-substituted acylating agent comprises a $C_{14}$ to $C_{28}$ alkenyl-substituted succinic anhydride.

* * * * *